United States Patent [19]
White

[11] Patent Number: 5,478,313
[45] Date of Patent: Dec. 26, 1995

[54] NEEDLE SHIELD

[76] Inventor: Jennifer A. White, 53 Putnam Ave., Cambridge, Mass. 02138

[21] Appl. No.: 292,312

[22] Filed: Aug. 18, 1994

[51] Int. Cl.$^6$ ..................................................... A61M 5/32
[52] U.S. Cl. ........................... 604/110; 604/192; 604/263
[58] Field of Search ..................... 604/110, 192, 604/198, 263, 164, 165

[56] References Cited

U.S. PATENT DOCUMENTS

| | | |
|---|---|---|
| 4,725,267 | 2/1988 | Vaillancourt ........................ 604/192 |
| 4,917,672 | 4/1990 | Terndrup et al. ..................... 604/192 |
| 4,921,490 | 5/1990 | Spier et al. ........................... 604/192 |
| 5,015,240 | 5/1991 | Soproni et al. ....................... 604/192 |
| 5,186,712 | 2/1993 | Kelso et al. .......................... 604/165 |
| 5,295,963 | 3/1994 | Deeks ............................... 604/263 X |
| 5,314,503 | 5/1994 | Bobrove et al. ....................... 604/164 |
| 5,360,408 | 11/1994 | Vaillancourt ......................... 604/198 |

*Primary Examiner*—John D. Yasko
*Attorney, Agent, or Firm*—John E. Troupal; Harold G. Jarcho

[57] ABSTRACT

A medical device including a needle having a substantially rectilinear shank portion joining a base and a tip for penetrating the skin of a patient; and an elongated tubularly wound coiled spring member having a compressible inner length portion with an end fixed to the base and a tubular outer length portion formed by engaged longitudinally distributed coils, the spring member having a normal length greater than the combined length of the shank portion and tip, the outer length portion having an arcuate normal shape, and the spring member defining a tube receiving the shank portion with the inner length portion compressed against the base so as to expose the tip and the outer length portion deformed from its arcuate normal shape into a substantially rectilinear shape by engagement with the shank portion. Also included is a latch engaging the spring member to retain the inner length portion compressed against the base and releaseable to allow expansion of the inner length portion, movement of the outer length portion over the tip, and return of the outer length portion to its normal arcuate shape with an outer end thereof displaced transversely from the tip.

26 Claims, 3 Drawing Sheets

NEEDLE SHIELD

BACKGROUND OF THE INVENTION

This invention relates generally to a medical device and, more specifically, to a medical device that prevents inadvertent punctures with contaminated needles.

Among the most frequently reported personnel injuries in hospitals are accidental needlesticks. Such needlesticks commonly occur when the sharp portion of a needle unintentionally enters the skin of healthcare personnel following the needle's use on a patient. Serious blood borne diseases including AIDS or hepatitis B can be transmitted to the healthcare personnel through an accidental needlestick following a needle's use on an infected patient.

The period of greatest risk for serious accidental needlestick injuries occurs after a patient has been penetrated and before a needle is discarded. Proper disposal of a used needle usually ends by discarding the needle into a hard-walled plastic container. Prior to discarding the needle, it may be recapped, broken, or removed from its attachment site on, for example, a catheter or syringe. Needlestick injuries commonly occur to the heatlthcare personnel while they are performing these tasks. When used needles are disposed of improperly, hospital maintenance and laundry staff are also at risk of sustaining needlestick injuries.

Because of the serious risk of inadvertent needle-punctures, there is a clear need to improve the process of disposing of used needles such that the risk of disease transmission attributed to accidental needlestick injuries to healthcare personnel is reduced. Various attempts to reduce the risk of needlestick injuries have focussed on either redesigning needle caps or adding recapping apparatus. Other attempts to alleviate the problem have focussed on redesigning medical devices used with the needles. Typical needle protection systems are disclosed, for example, in U.S. Pat. Nos. 4,725,267; 4,917,672; 4,921,490 and 5,015,240. The disadvantages of prior approaches are that they are complex and expensive to manufacture. They are also limited in their application to a wide variety of needle types and sizes.

The object of this invention, therefore, is to provide improved, inexpensive medical devices that facilitate safe disposal of used needles.

SUMMARY OF THE INVENTION

The invention is a medical device including a needle having a substantially rectilinear shank portion joining a base and a tip for penetrating the skin of a patient; and an elongated tubularly wound coiled spring member having a compressible inner length portion with an end fixed to the base and a tubular outer length portion formed by engaged longitudinally distributed coils, the spring member having a normal length greater than the combined length of the shank portion and tip, the outer length portion having an arcuate normal shape, and the spring member defining a tube receiving the shank portion with the inner length portion compressed against the base so as to expose the tip and the outer length portion deformed from its arcuate normal shape into a substantially rectilinear shape by engagement with the shank portion. Also included is a latch engaging the spring member to retain the inner length portion compressed against the base and releaseable to allow expansion of the inner length portion, movement of the outer length portion over the tip, and return of the outer length portion to its normal arcuate shape with an outer end thereof displaced transversely from the tip. After release of the latch, the outer length portion covers the tip to prevent inadvertent skin penetration thereby.

According to certain features of the invention, the latch includes a collar movable over the tip and the shank portion into latched engagement with the base, and the collar defines an internal cavity that receives the spring member. Preferably, the collar is shaped and arranged for press fitted engagement with a cylindrical portion of the base.

According to another feature of the invention, a latch is formed by an intravenous catheter having a hub coupling joined with a fluid flow tube, the tube being shaped and arranged for passing over the tip into fitted engagement with the shank portion, and the hub coupling forming the collar.

According to another feature of the invention, the outer end defines an opening, and the opening is displaced transversely from the tip after release of the latch. Transverse displacement inhibits penetration of the opening by the tip.

According to yet other features of the invention, the outer length portion is substantially cylindrical and incompressible and the coils are engaged along surfaces oriented substantially longitudinally. The longitudinally engaged coils prevent penetration of the outer length portion by the tip.

According to one embodiment of the invention the coils are formed of wire having a rectangular cross-section. Penetration of the outer length portion by the tip is inhibited by the coils of rectangular cross-section.

According to another embodiment of the invention, the outer length portion includes individual coils distributed and engaged both longitudinally and transversely so as to form a tubular section having multiple coil plies. Penetration of the outer length portion by the tip is inhibited by the engaged coil plies.

According to yet another embodiment of the invention, the outer length portion is substantially conical and the coils are formed by telescopically engaged sheet material. Penetration of the outer length portion by the tip is prevented by the engaged sheet material coils.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENTS

Figure 1:
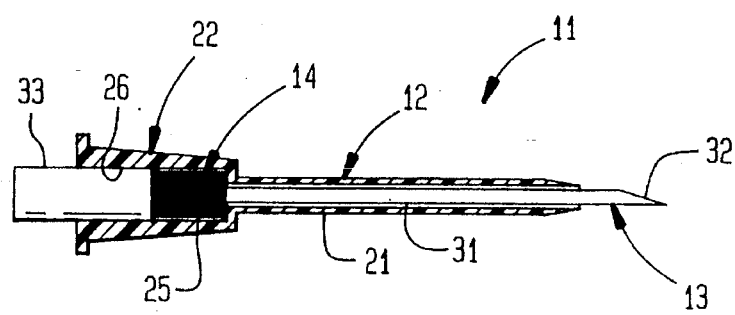
FIG. 1 is a cross-sectional view of a medical device of the invention with components in relative positions prior to use.

A medical device 11 is illustrated in FIG. 1. The device 11 includes an intravenous catheter 12 into which a needle 13 has been inserted. Also included in the device 11 is a spring shield member 14 which is fixed to the needle 13 and retained in an inactive position by the catheter 12 as described hereinafter.

The catheter 12 includes a fluid flow tube 21 extending from a collar hub 22 having a conically shaped outer surface 23. Formed internally at one end of the hub collar 22 is a cylindrical cavity 25. An internal cylindrical bore 26 at the other end of the hub collar 22 communicates with the cylindrical cavity 25.

The needle 13 has a shank portion 31 straddled by a sharpened needle tip 32 and a cylindrical base portion 33. As shown in FIG. 1, the shank portion 31 of the needle 13 is dimensioned so as to be closely received by the fluid flow tube 21. In addition, the cylindrical base portion 33 is dimensioned so as to accommodate a press fit with the cylindrical bore 26 of the collar hub 22.

Figure 2:
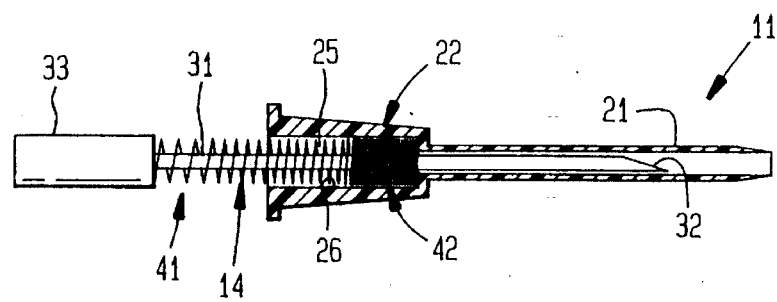
FIG. 2 is a cross-sectional view of the device shown in FIG. 1 but with components in relative positions during use.
Figure 3:
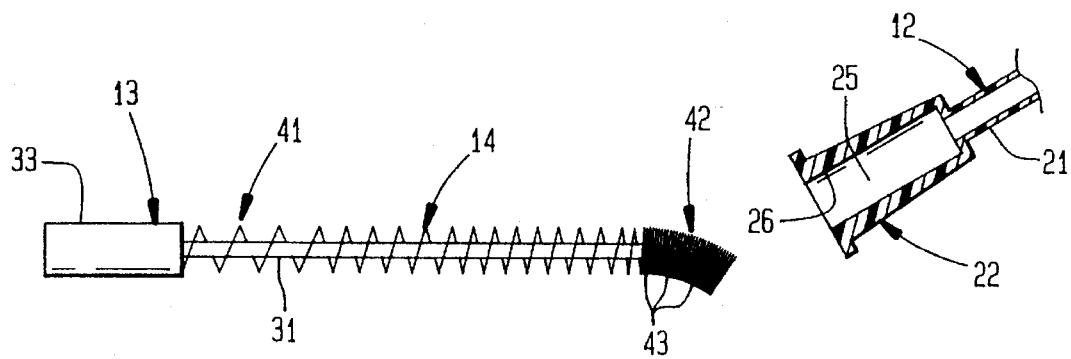
FIG. 3 is a cross-sectional view of the device shown in FIGS. 1 and 2 but with components in relative positions after use.

As shown in FIGS. 2 and 3, the spring member 14 is an elongated, tubularly wound coiled spring having an inner length portion 41 and an outer length portion 42. The inner length portion 41 is relatively loosely wound so as to be compressible and an end thereof is fixed to the cylindrical base portion 33 of the needle 13. Conversely, the outer length portion 42 of the member 14 is formed by longitudinally distributed, tightly wound engaging coils 43 so as to be substantially incompressible. In addition, the outer length portion 42 is formed so as to have a normally arcuate shape as illustrated in FIG. 3. The spring member 14 forms a tube having a normal length, including the inner length portion 41 and the outer length portion 42, which is greater than the combined length of the shank portion 31 and tip 32 of the needle 13 which are received thereby.

Prior to use of the medical device 11, the individual components thereof have the relative positions depicted in FIG. 1. Those relative positions are established by drawing the catheter 12 back on the needle 13 so as to expose the tip 32 and press fit the cylindrical base portion 33 into the cylindrical bore 26. During that assembly of the device 11, the hub collar 22 engages the spring member 14 to compress the inner length portion 41 thereof against the cylindrical base portion 33 of the needle 13 and thereby expose the tip 32. With the cylindrical bore 26 press fitted over the cylindrical base portion 33 of the needle 13, the hub collar 22 latches the spring member 14 into the contracted condition shown in FIG. 1 with the inner length portion 41 compressed against the base portion 33 and the outer length portion 42 deformed into a relatively rectilinear shape by engagement with the shank portion 31 of the needle 13.

During use, the medical device 11 is inserted into a patient with the needle tip 32 leading penetrating movement. After proper insertion, the latching effect of the hub collar 22 is released by slowly withdrawing the needle 13 and attached spring member 14 from the catheter 12 in the manner shown in FIG. 2. During withdrawal movement of the needle 13, the compressed inner length portion 41 expands to increase the length of the spring member 14 to assume its normal length and the outer length portion 42 assuming its normal arcuate shape and extending over the needle tip 13. Pursuant to removal of the needle 13 and spring member 14, the catheter 12 is used in a conventional manner to provide intravenous fluid flow into a patient.

Figure 4:
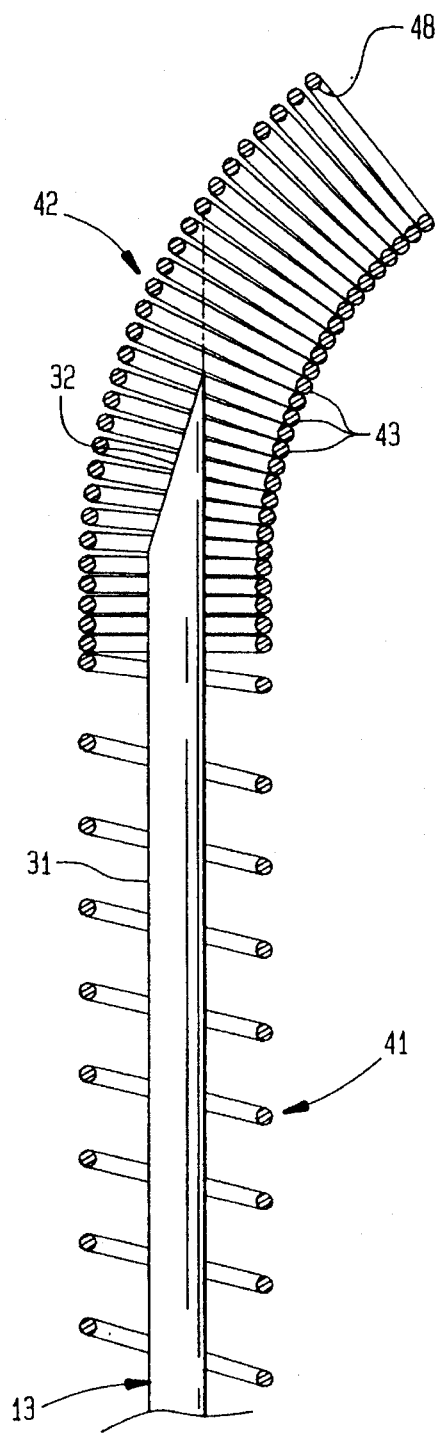
FIG. 4 is an expanded sectional view of the device with components in the positions shown in FIG. 3.

FIG. 4 illustrates more clearly the relative positions of the needle 13 and spring member 14 after removal from the intravenous catheter assembly 12. As shown, inner length portion 41 of the spring member 14 is expanded into a normal state and the outer length portion 42 has moved over the tip 32 of the needle 13. In addition, a memory produced during formation of the spring member 13 has caused the outer length portion 42 to assume its normal arcuate shape with an opening 48 at an outer end thereof laterally displaced from the needle tip 32. Because of that displacement, the needle tip 32 is covered by the tube formed by the closely adjacent, longitudinally distributed coils 43. Thus, after use of the needle 13, the outer spring tube portion 42 functions as a shield to prevent inadvertent skin penetration by the needle point 32.

Figure 5:
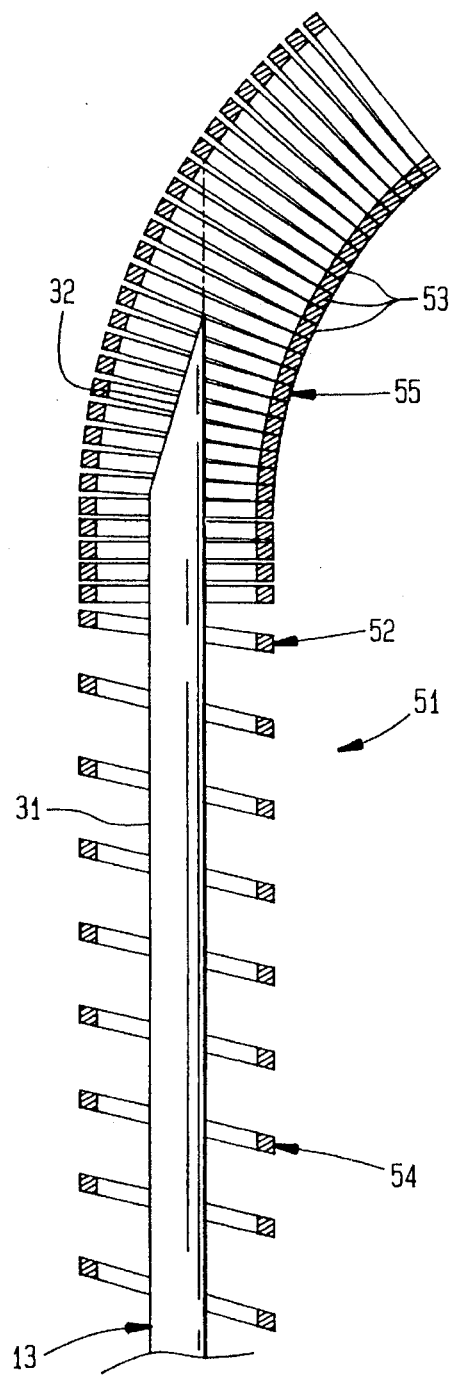
FIG. 5 is a partial cross-sectional view of another embodiment of the invention.

FIG. 5 illustrates another medical device embodiment 51 that is used in the same manner as the embodiment 11. Components of the device 51 which are identical to those of the embodiment 11 have been given the same reference numerals. The embodiment 51 is identical to the embodiment 11 except that a spring member 52 is composed of longitudinally distributed coils 53 formed with a wire 54 having a rectangular cross-section rather than the circular cross-section used for the spring member 14 of device 11. The wire 54 provides for the coils 53 planar surfaces that after contact with the needle point 32 impair any tendency thereof to penetrate between longitudinally engaging, adjacent coils 53 of an outer length portion 55.

Figures 6, 7:
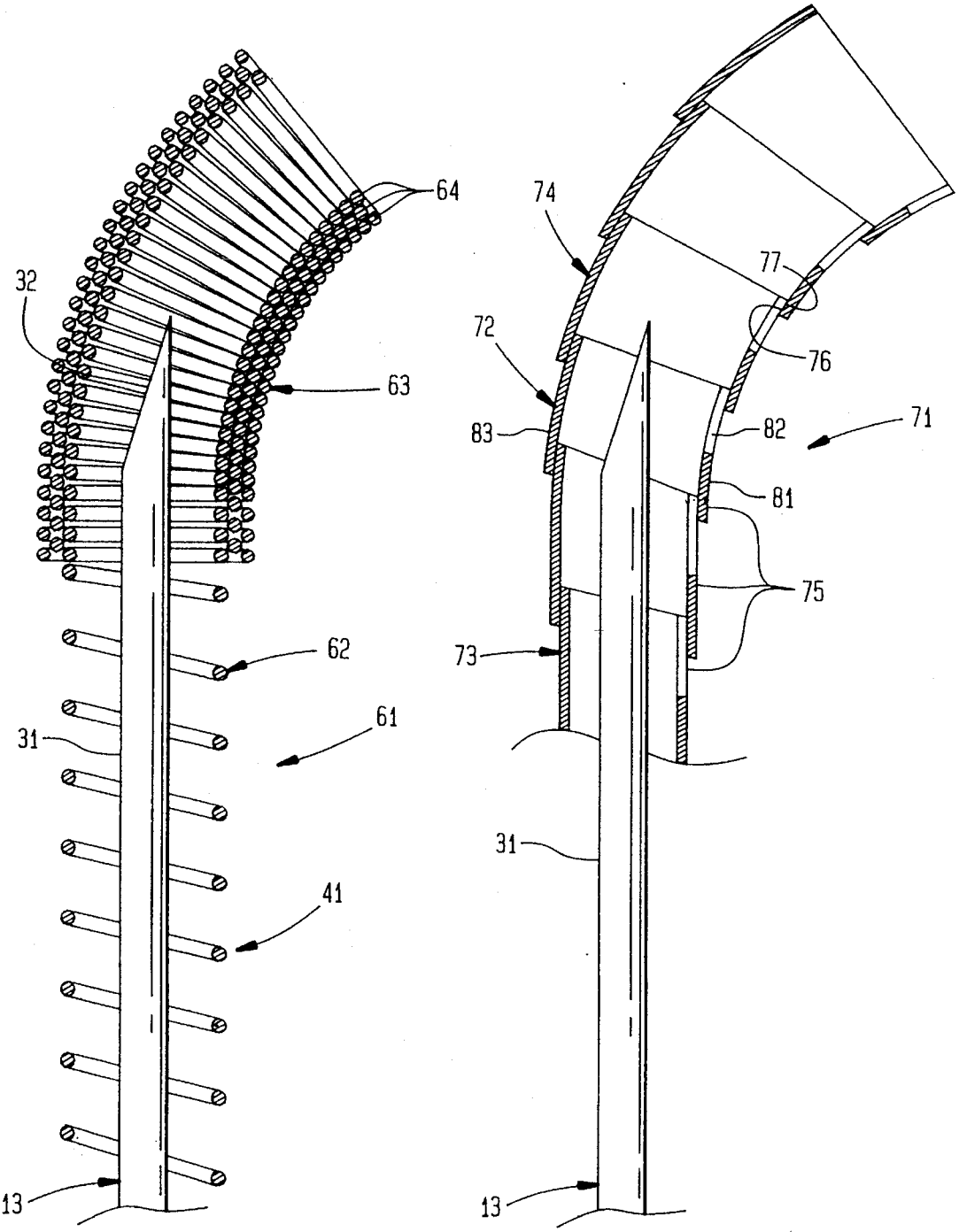
FIG. 6 is a partial cross-sectional view of another embodiment of the invention.
FIG. 7 is a partial cross-sectional view of another embodiment of the invention.

FIG. 6 illustrates another medical device embodiment 61 that is used in the same manner as the embodiment 11. Components of the device 61 which are identical to those of the device 11 again have been given the same reference numerals. The device 61 is identical to the device 11 except for the use of a modified spring member 62. As shown in FIG. 6, the outer spring length portion 42 of embodiment 11 has been replaced by a modified outer spring length portion 63. Forming the outer spring length 63 of the spring member 62 are a plurality of varied diameter, interconnected coils 64 distributed and engaged both longitudinally and transversely to form a tubular section of multiple coil plies. The plies of the outer length spring portion 63 provide multiple abutting surfaces which further restrict any tendency of the needle tip 32 to penetrate between the adjacent coils 64.

FIG. 7 illustrates another medical device embodiment 71 that is used in the same manner as the embodiment 11. Again, components of the device 71 which are identical to those of the device 11 have been given the same reference numerals. The device 71 is identical to the device 11 except that the spring member 14 has been replaced by a modified spring member shield 72 having a rectilinear conically shaped inner length portion 73 and an arcuate, conically shaped outer length portion 74. Forming each of the inner and outer length portions 73, 74, respectively, are interconnected coils 75 formed of sheet spring material and telescopically engaged along transversely oriented surface 76, 77. Penetration of the outer length portion 74 by the needle tip 32 is prevented by the engaged surfaces 76, 77 of the coils 75. To facilitate bending of the outer length portion 74 into the arcuate shape shown in FIG. 7, concave length portions 81 of the coils 75 are provided with longitudinal slots 82 that shorten the concave length portions with respect to convex length portions 83 disposed diametrically opposite thereto.

Obviously, many modifications and variations of the present invention are possible in light of the above teachings. It is to be understood, therefore, that the invention can be practiced otherwise than as specifically described.

What is claimed is:

1. A medical device comprising:

needle means having a substantially rectilinear shank portion joining a base means and a tip for penetrating the skin of a patient;

an elongated tubularly wound coiled spring member having a compressible inner length portion with an end fixed to said base means and a tightly wound substantially incompressible tubular outer length portion formed by a plurality of longitudinally distributed coils, said spring member having a normal length greater than the combined length of said shank portion and said tip and said outer length portion having an arcuate normal shape, and said spring member defining a tube receiving said shank portion with said inner length portion compressed against said base means so as to expose said tip and said outer length portion deformed from said arcuate normal shape into a substantially rectilinear shape by engagement with said shank portion; and latch means engaging said spring member to retain said inner length portion compressed toward said base means and releasable to allow expansion of said inner length portion, movement of said outer length portion over said tip, and return of said outer length portion to said normal arcuate shape with an outer end thereof displaced transversely from said tip.

2. A medical device according to claim 1 wherein said latch means comprises a collar movable by said tip and over said shank portion into latched engagement with said base means, said collar defining an internal cavity that receives said spring member.

3. A medical device according to claim 2 wherein said collar is shaped and arranged for press fitted engagement with said base means.

4. A medical device according to claim 3 wherein said latch means comprises an intravenous catheter having a hub coupling joined with a fluid flow tube, said tube being shaped and arranged for passing over said tip into fitted engagement with said shank portion, and said hub coupling forming said collar.

5. A medical device according to claim 1 wherein said coils are formed by wire having a rectangular cross-section.

6. A medical device according to claim 5 wherein said latch means comprises a collar movable by said tip and over said shank portion into latched engagement with said base means, said collar defining an internal cavity that receives said spring member.

7. A medical device according to claim 6 wherein said collar is shaded and arranged for press fitted engagement with said base means.

8. A medical device according to claim 7 wherein said latch means comprises an intravenous catheter having a hub coupling joined with a fluid flow tube, said tube being shaped and arranged for passing over said tip into fitted engagement with said shank portion, and said hub coupling forming said collar.

9. A medical device according to claim 1 wherein said outer length portion comprises individual coils distributed and engaged both longitudinally and transversely so as to form a tubular section having multiple coil plies.

10. A medical device according to claim 9 wherein said latch means comprises a collar movable by said tip and over said shank portion into latched engagement with said base portion, said collar defining an internal cavity that receives said spring member.

11. A medical device according to claim 10 wherein said collar is shaped and arranged for press fitted engagement with said base means.

12. A medical device according to claim 11 wherein said latch means comprises an intravenous catheter having a hub coupling joined with a fluid flow tube, said tube being shaped and arranged for passing over said tip into fitted engagement with said shank portion, and said hub coupling forming said collar.

13. A medical device according to claim 1 wherein said outer end defines an opening, and said opening is displaced transversely from said tip after release of said latch means.

14. A medical device according to claim 13 wherein said latch means comprises a collar movable by said tip and over said shank portion into latched engagement with said base portion, said collar defining an internal cavity that receives said spring member.

15. A medical device according to claim 14 wherein said collar is shaped and arranged for press fitted engagement with said base means.

16. A medical device according to claim 15 wherein said latch means comprises an intravenous catheter having a hub coupling joined with a fluid flow tube, said tube being shaped and arranged for passing over said tip into fitted engagement with said shank portion, and said hub coupling forming said collar.

17. A medical device according to claim 1 wherein said tubular outer length portion is substantially cylindrical and said coils are engaged along surfaces oriented substantially longitudinally.

18. A medical device according to claim 17 wherein said latch means comprises a collar movable by said tip and over said shank portion into latched engagement with said base means, said collar defining an internal cavity that receives said spring member.

19. A medical device according to claim 18 wherein said collar is shaded and arranged for press fitted engagement with said base means.

20. A medical device according to claim 19 wherein said latch means comprises an intravenous catheter having a hub coupling joined with a fluid flow tube, said tube being shaped and arranged for passing over said tip into fitted engagement with said shank portion, and said hub coupling forming said collar.

21. A medical device according to claim 1 wherein said tubular outer length portion is substantially conical and said coils are engaged along transversely oriented surfaces.

22. A medical device according to claim 21 wherein said coils are formed of sheet material engaged telescopically.

23. A medical device according to claim 22 wherein each of said coils forming said outer length portion have a longitudinally extending convex length portion and a longitudinally extending concave length portion disposed diametrically opposite to said convex length portion, and said concave length portion of at least some of said coils is shorter than its said convex length portion.

24. A medical device according to claim 23 wherein said latch means comprises a collar movable by said tip and over said shank portion into latched engagement with said base means, said collar defining an internal cavity that receives said spring member.

25. A medical device according to claim 24 wherein said collar is shaped and arranged for press fitted engagement with said base means.

26. A medical device according to claim 25 wherein said latch means comprises an intravenous catheter having a hub coupling joined with a fluid flow tube, said tube being shaped and arranged for passing over said tip into fitted engagement with said shank portion, and said hub coupling forming said collar.

* * * * *